US007828757B2

(12) United States Patent
Blocker

(10) Patent No.: US 7,828,757 B2
(45) Date of Patent: Nov. 9, 2010

(54) AIR FLOW SLEEVE SYSTEM AND CAST STRUCTURE INCORPORATING AIR FLOW SLEEVE SYSTEM

(76) Inventor: Tyrone Blocker, 5928 NE. 33rd Ave., Portland, OR (US) 97211

( * ) Notice: Subject to any disclaimer, the term of this patent is extended or adjusted under 35 U.S.C. 154(b) by 170 days.

(21) Appl. No.: 11/974,297

(22) Filed: Oct. 12, 2007

(65) Prior Publication Data
US 2008/0039754 A1 Feb. 14, 2008

Related U.S. Application Data

(63) Continuation-in-part of application No. 11/367,502, filed on Mar. 2, 2006, now abandoned.

(60) Provisional application No. 60/851,505, filed on Oct. 13, 2006.

(51) Int. Cl.
A61F 5/00 (2006.01)
A61H 7/00 (2006.01)

(52) U.S. Cl. ............................. 602/2; 601/11

(58) Field of Classification Search ............. 602/1, 602/2, 3, 13, 69, 14; 128/91, 83, 89, 90; 601/11, 135, 16, 17, 148; 604/307; 607/108, 607/112
See application file for complete search history.

(56) References Cited

U.S. PATENT DOCUMENTS

| 432,899 | A | 7/1890 | Reenstierka | |
|---|---|---|---|---|
| 3,701,349 | A | 10/1972 | Larson | |
| 4,019,506 | A | 4/1977 | Eschmann | |
| 4,308,862 | A | 1/1982 | Kalmar | |
| 4,387,710 | A | 6/1983 | Beatty | |
| 4,898,160 | A | 2/1990 | Brownlee | |
| 6,053,882 | A | * | 4/2000 | Johansen ............. 602/14 |
| 6,120,469 | A | | 9/2000 | Bruder |
| 6,547,751 | B1 | | 4/2003 | Barberio |
| 6,616,622 | B1 | | 9/2003 | Barberio |
| 2004/0039317 | A1 | * | 2/2004 | Souney et al. ......... 602/13 |
| 2004/0162511 | A1 | * | 8/2004 | Barberio ............. 602/14 |
| 2004/0230148 | A1 | * | 11/2004 | Barberio ............. 602/3 |
| 2005/0059915 | A1 | * | 3/2005 | Dunagan ............. 602/14 |
| 2005/0203451 | A1 | | 9/2005 | Reis et al. |

FOREIGN PATENT DOCUMENTS

DE 3442739 5/1986
EP 0346697 12/1989

* cited by examiner

Primary Examiner—Patricia M Bianco
Assistant Examiner—Tarla R Patel
(74) Attorney, Agent, or Firm—Law Office of Karen Dana Oster

(57) ABSTRACT

An air flow sleeve system for injecting air flow from an air producing mechanism into a cast system preferably includes an air flow sleeve having at least one aperture through which air may flow. A separator is preferably positioned within the air flow sleeve such that it is at least partially longitudinally coextensive with the air flow sleeve. The air flow sleeve may be used with a coupler that may be integrated with the cast system. Preferred embodiments of the cast system include casting material, a comfort layer, and a backing/padding layer. When air from the air producing mechanism flows into the air flow sleeve, the air flow sleeve expands. The backing/padding layer compacts to allow the expansion of the air flow sleeve. The present invention also includes a method for creating a cast structure including the air flow sleeve.

13 Claims, 8 Drawing Sheets

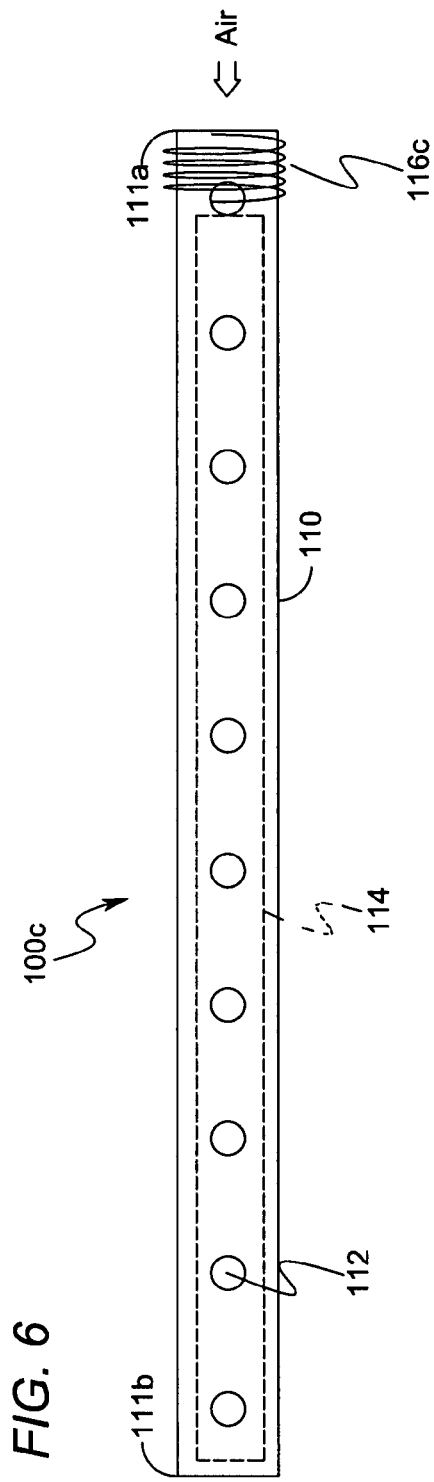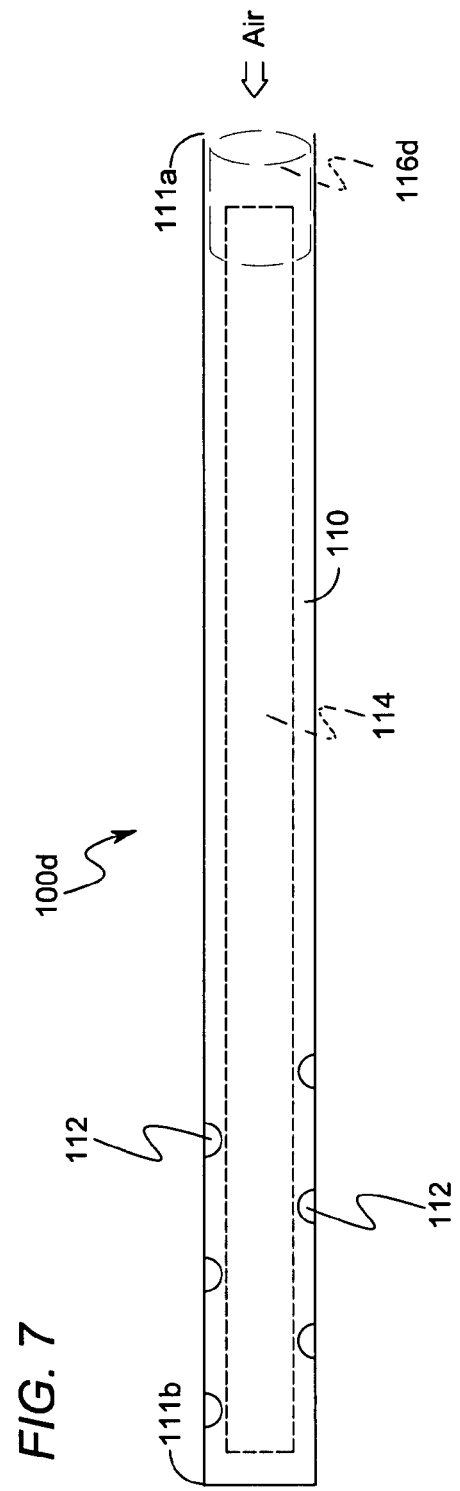

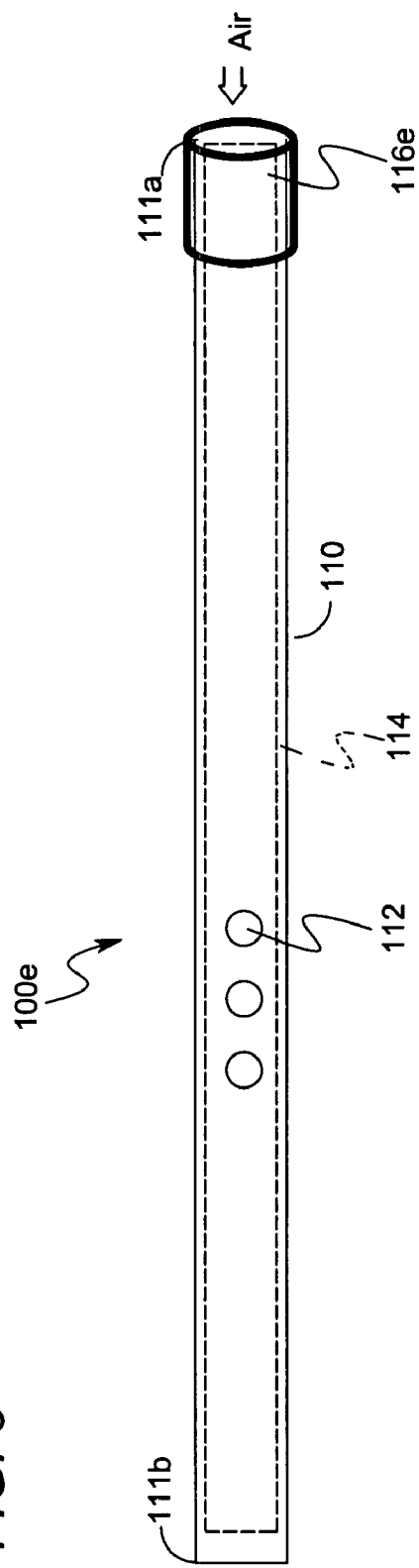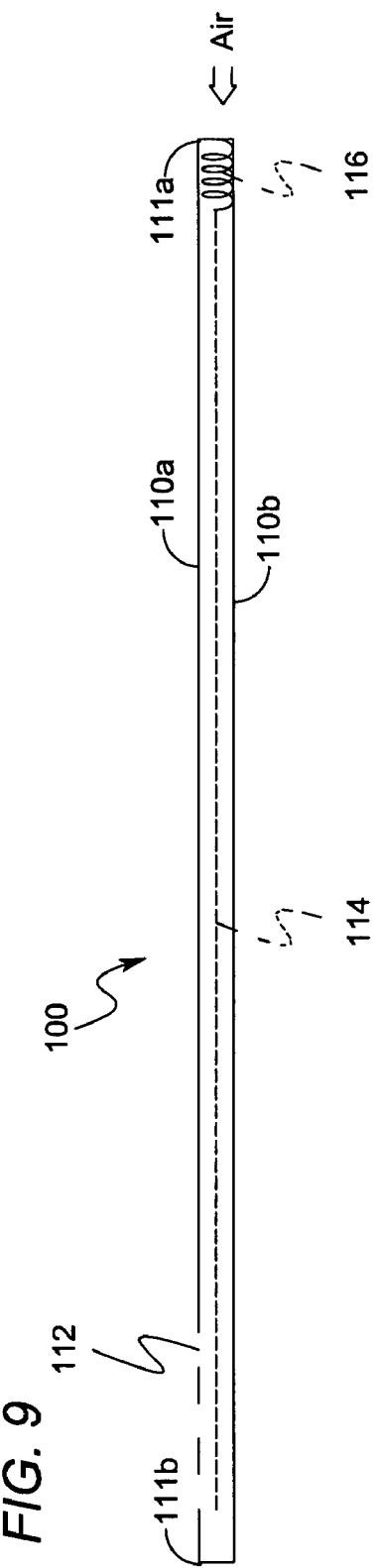

AIR FLOW SLEEVE SYSTEM AND CAST STRUCTURE INCORPORATING AIR FLOW SLEEVE SYSTEM

The present application is an application claiming the benefit under 35 USC Section 119(e) of U.S. Provisional Patent Application Ser. No. 60/851,505, filed Oct. 13, 2006. The present application is a continuation-in-part of U.S. patent application Ser. No. 11/367,502, filed Mar. 2, 2006. The present application is based on and claims priority from these applications, the disclosures of which are hereby expressly incorporated herein by reference.

BACKGROUND OF INVENTION

The present invention is directed to an air flow sleeve system used to inject air flow into a cast and a cast structure incorporating the air flow sleeve system.

A cast holds a broken bone in place as it heals. In general, casts immobilize the joint above and the joint below the area that is to be kept straight and without motion. The outside, or hard part of the cast, may be made from casting materials such as plaster or fiberglass. Cotton (e.g. cotton undercast padding), orthopedic stockinettes, synthetic materials, waterproof materials, and other liners may be used to line the inside of the cast to make it more comfortable. However, patients still find that the body part (generally a limb) immobilized by the cast sill tend to be hot, tend to itch, or otherwise tend to be uncomfortable.

For many years there was no efficient medical treatment for the problems associated with casting such as itching. Patients suffering from the itchy side-effects of the cast were advised to take anti-itch drugs (e.g. Benadryl®). Most patients found little or no relieve from the anti-itch drugs. Some patients found the anti-itch drugs had other side effects (e.g. drowsiness). Some patients were allergic to the anti-itch drugs. Finding no relief from the anti-itch drugs, patients resorted to their own treatments.

One popular patient treatment to which suffering patients resorted was to insert foreign objects (e.g. rulers, wire clothing hangers, and dowels) into the cast. Although this might relieve the itching, there was a high risk of skin irritation, scrapes, cuts, infections (e.g. staphylococcal infections that could result in possible amputation of the casted body part), and damage to cast. In some cases the itching inside the cast becomes so intense, that patients removed the cast prematurely (sometimes by themselves and sometimes with a doctor's assistance) before the fracture or broken bone had properly healed. Premature removal of a cast can result in the fracture or broken bone relocating (which could cause permanent injury). Premature removal of the cast can also require additional visits to the hospital and/or added expenses.

Recognizing the discomfort suffered as a result of casts, attempts have been made to alleviate the discomfort. One such product is "CastBlast™." CastBlast™ is an aerosol can that is used to inject a talc spray that is supposed to cool and soothe the skin covered by the cast. Another product is a cast ventilation system that is described in U.S. Pat. No. 6,120,469 to Bruder (the "Bruder reference"). The Bruder cast ventilation system is a tube insertable through an opening in the cast so that one end of the tube is open to the limb while the other end of the tube is open to the outside surface of the cast. A source of pressurized air is then fluidly connected to the outer end of the tube so that, upon activation of the pressurized air source, the pressurized air source blows air into the area between the inside of the cast and the limb. The Bruder reference states that air flow dries or removes any moisture which may be present on the inside surface of the cast.

U.S. Pat. No. 6,053,882 to Johansen (the "Johansen reference") is directed to a cast ventilation sleeve for reducing skin irritation and odor associated with broken limbs that are immobilized for significant periods of time by casts or the like. The ventilation sleeve is an elongated flexible bag that is positioned between the cast and the skin of a limb. Specifically, the Johansen reference shows the ventilation sleeve is positioned between fabric (specifically an orthopedic stockinettes) surrounding a limb and the cast. The ventilation sleeve, when installed, is in a collapsed (un-inflated) condition such that its thickness is essentially the same as the width of the material used to make the ventilation sleeve. When air is introduced to the ventilation sleeve, the ventilation sleeve expands to an expanded condition. One side of the ventilation sleeve flexible bag has a plurality of ventilation openings through which pressurized air aerates the cast. The plurality of ventilation openings is arranged substantially along the length of the bag of the ventilation sleeve, the length of the flexible bag being dimensioned to be substantially equal to the length of the cast. An orifice and fitting (that, in one embodiment, protrudes from one end of the cast) lead into the flexible bag to provide an entrance to introduce air into the flexible bag. The fitting permits the attachment of an air tube for delivering pressurized air from a compressor to the ventilation sleeve. The air expands the flexible bag and flows out through the plurality of ventilation openings.

BRIEF SUMMARY OF THE INVENTION

The present invention is directed to an air flow sleeve system for injecting air flow from an air producing mechanism into a cast system. The air flow sleeve system preferably includes an air flow sleeve having at least one aperture through which air may flow. A separator is preferably positioned within the air flow sleeve such that it is at least partially longitudinally coextensive with the air flow sleeve.

The air flow sleeve may be used with a coupler having an input air insertion end functionally connectable to the air producing mechanism and an output sleeve end functionally connectable to the accessible end of the air flow sleeve. The coupler may be integrated with the cast system.

Preferred embodiments of the cast system include casting material, a comfort layer, and a backing/padding layer. When air from the air producing mechanism flows into the air flow sleeve, the air flow sleeve expands. The backing/padding layer compacts to allow the expansion of the air flow sleeve.

The present invention also includes a method for creating a cast structure including the air flow sleeve.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 6 is a top plan view of a third exemplary preferred embodiment of an inflatable air flow sleeve system having a plurality of apertures on the air flow sleeve and an exterior spring retaining device.

FIG. 7 is a top plan view of a fourth exemplary preferred embodiment of an inflatable air flow sleeve system having groupings of apertures on the sides of the air flow sleeve at the encased end of the air flow sleeve and an interior alternative retaining device.

FIG. 8 is a top plan view of a fifth exemplary preferred embodiment of an inflatable air flow sleeve system having a single grouping of apertures towards the longitudinal middle of the air flow sleeve and an exterior alternative retaining device.

FIG. 9 is a side view of an exemplary preferred embodiment of an inflatable air flow sleeve system having a single grouping of apertures in the top sleeve sheet at the encased end of the air flow sleeve.

DETAILED DESCRIPTION OF THE INVENTION

Figure 1:
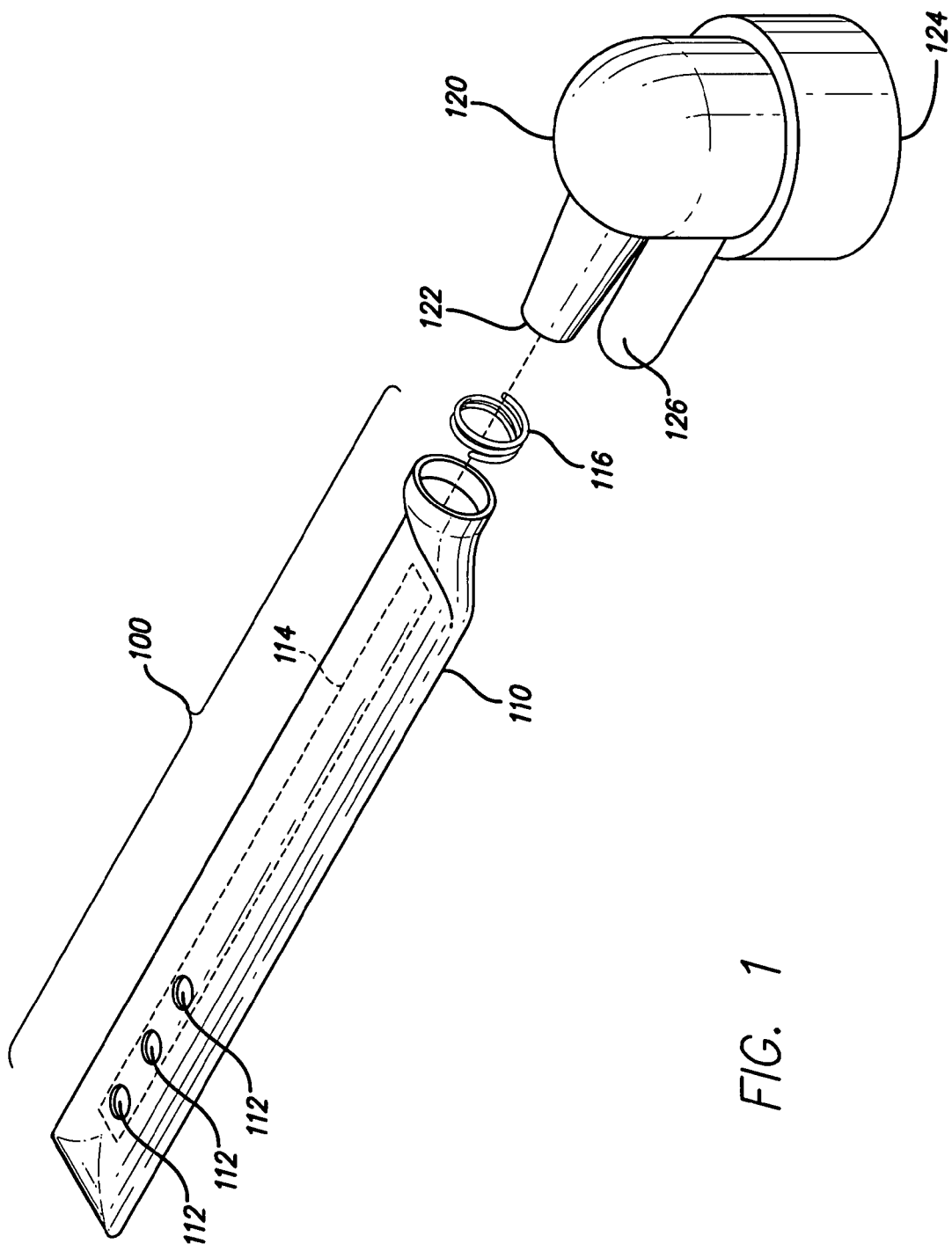
FIG. 1 is an expanded perspective view of an exemplary preferred embodiment of an inflatable air flow sleeve system of the present invention and an exemplary unique coupler.

As shown in the figures, the present invention is directed to an air flow sleeve system 100 (FIG. 1) used to inject airflow into a cast system 140 (FIGS. 2 and 3), the air flow sleeve system 100 and the cast system 140 together forming a cast structure. Exemplary preferred embodiments of the air flow sleeve system 100 (as shown in FIGS. 4-12) include, for example, an inflatable air flow sleeve 110 having at least one aperture 112 (hole) defined therein, a separator 114, and a retaining device 116. In one preferred embodiment, the air flow sleeve system 100 mates with a unique coupler 120. The unique coupler 120 connects one end of the air flow sleeve 110 to an air producing mechanism 130 either directly or via air transmitting structure 132. The air flow sleeve system 100 of the present invention is preferably incorporated into a cast system 140 (of which the casting material 102 is one component) to form a unique cast structure. When air is injected into the air flow sleeve system 100, the air flow sleeve 110 at least partially inflates. Air then escapes through the apertures 112 and is forced towards and around the limb to provide a means for relieving the itching inside the patient's cast system 140 naturally and without the possibility of side effects, infections, or injury. The present invention also preferably provides heat relief, reduces moisture, and reduces bacteria build-up inside the cast system 140.

Air Flow Sleeve and Apertures

Preferred embodiments of the air flow sleeve system 100 include an inflatable air flow sleeve 110 having at least one aperture 112 (hole) defined therein. The air flow sleeve 110 has a first accessible end 111a and a second encased end 111b. The term "accessible" refers to a user's ability to access the end 111a (which may be protruding from the cast system 140, at the edge of the cast system 140 (as shown), or slightly within the cast system 140) after the air flow sleeve 110 has been integrated into a cast system 140. The term "encased" refers to the fact that the end 111b is preferably encased in, covered by, and/or enclosed within the cast system 140. As shown in the exemplary embodiments shown in side view (i.e. FIGS. 9-11 being uninflated and FIG. 12 being inflated), one preferred embodiment of the air flow sleeve 110 has a substantially flat configuration that includes a top sleeve sheet 110a and a bottom sleeve sheet 110b, at least one "sleeve sheet" 110a, 110b having apertures 112 therein. (It should be noted that the terms "top" and "bottom" are meant to be relative terms used to describe the invention in terms relative to the shown drawings and are not meant to limit the scope of the invention.) It should be noted that the preferred embodiment of the air flow sleeve 110 is substantially flat when not inflated. Accordingly, it will be appreciated that the side view drawings may be considered exaggerated in thickness as there is an exaggerated space between the top sleeve sheet 110a and the bottom sleeve sheet 110b.

The air flow sleeve 110 may be constructed using a wide variety of methods and/or materials. The air flow sleeve 110 may be constructed using of two separate "sleeve sheets" that are joined (e.g. connected, adhered, bonded) on longitudinal sides (and preferably the second encased end 111b). The air flow sleeve 110 may be constructed using of a single sheet of material that is folded longitudinally and joined on the non-folded longitudinal side (and preferably the second encased end 111b). The air flow sleeve 110 may be constructed using tubular material that may be flattened (and preferably joined at the second encased end 111b). A "substantially flat" configuration is preferable for the ease in which the cast system 140 may be formed around it, but it should be noted that the material is preferably flexible and/or shape-conformable such that it is able to substantially follow the contours of the limb upon which it being used. It should be noted, that the material from which the air flow sleeve 110 is to be constructed may be plastic or other materials that are suitably flexible, shape-conformable, durable, and/or of the appropriate medical grade or having the appropriate qualities necessary for fulfilling their function. These examples are meant to suggest alternatives and are for purposes of enablement, but the examples are not meant to limit the scope of the invention.

Figure 4:
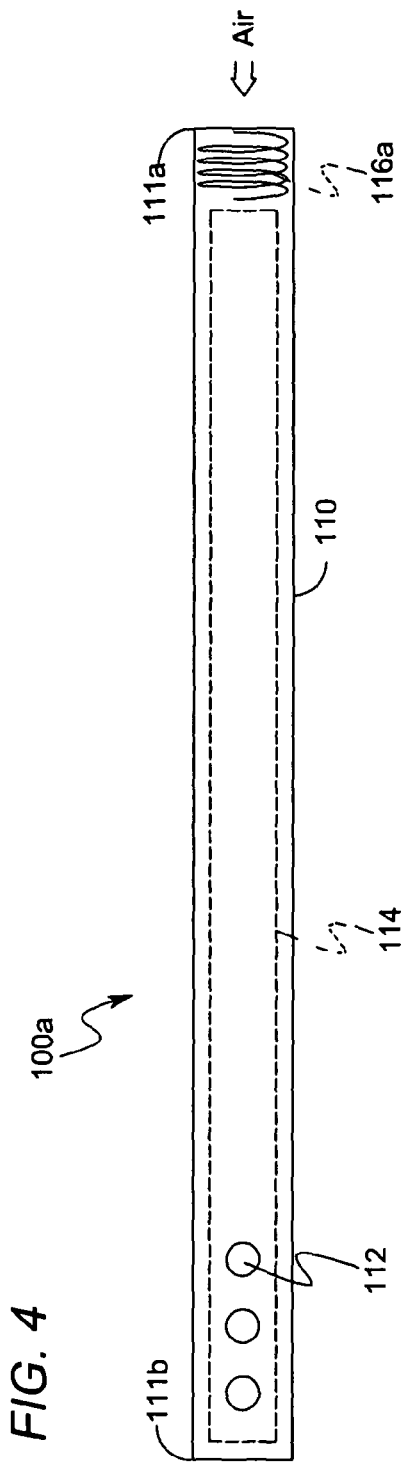
FIG. 4 is a top plan view of a first exemplary preferred embodiment of an inflatable air flow sleeve system having a single grouping of apertures at the encased end of the air flow sleeve and an interior spring retaining device.
Figure 5:
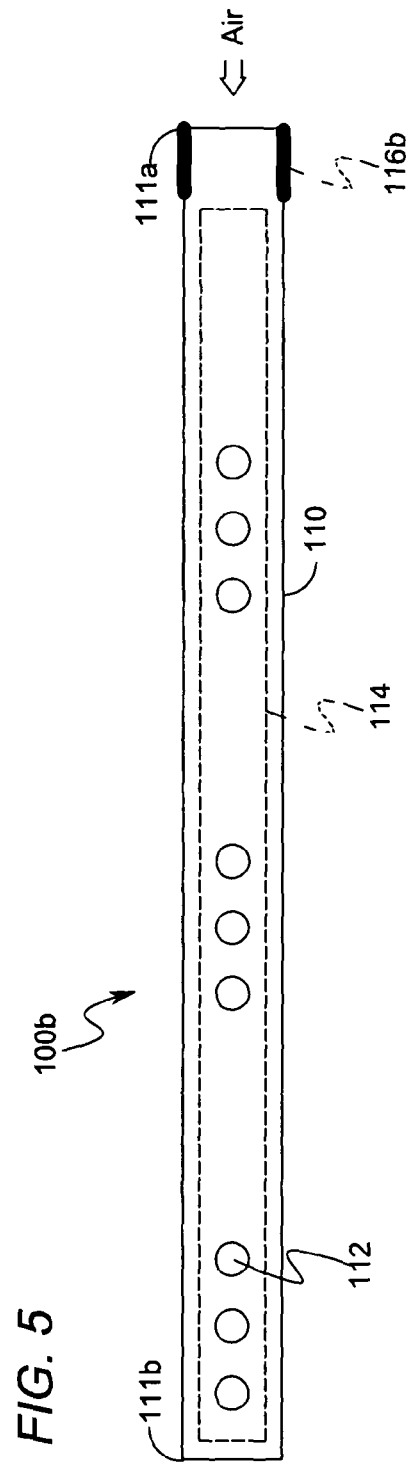
FIG. 5 is a top plan view of a second exemplary preferred embodiment of an inflatable air flow sleeve system having a plurality of groupings of apertures on the air flow sleeve and a reinforcement retaining device.
Figure 10:
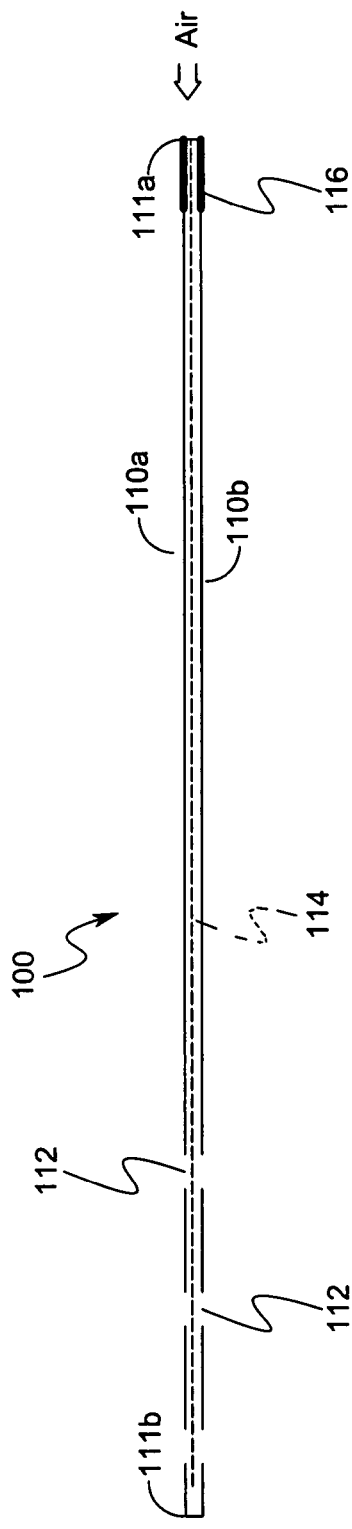
FIG. 10 is a side view of an exemplary preferred embodiment of an inflatable air flow sleeve system having groupings of apertures in the top sleeve sheet and the bottom sleeve sheet at the encased end of the air flow sleeve, the grouping of apertures in the top sleeve sheet being directly opposite the grouping of apertures the bottom sleeve sheet.
Figure 11:
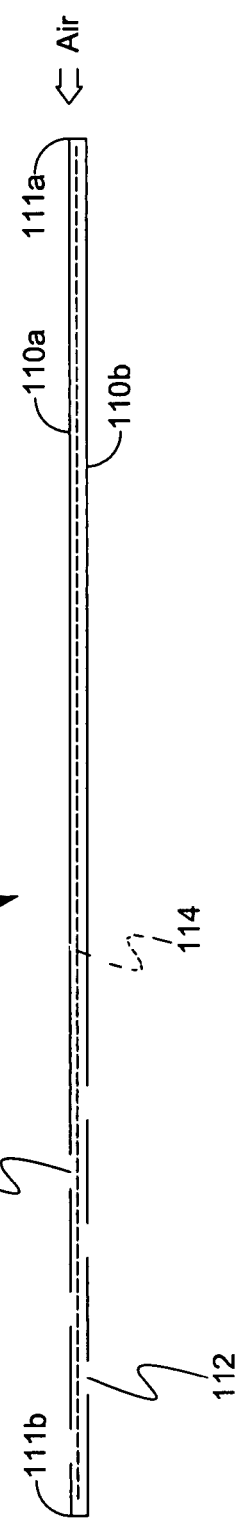
FIG. 11 is a side view of an exemplary preferred embodiment of an inflatable air flow sleeve system having groupings of apertures in the top sleeve sheet and the bottom sleeve sheet at the encased end of the air flow sleeve, the grouping of apertures in the top sleeve sheet being staggered from the grouping of apertures the bottom sleeve sheet.

Regarding the apertures 112, there are many configurations and arrangements that would function with different degrees of effectiveness. The following are meant to be exemplary and are not meant to limit the scope of the invention. As shown in FIG. 4, in some preferred embodiments of the invention a single grouping (i.e. a plurality of apertures positioned relatively close together and relatively remote from other apertures) of apertures 112 is positioned at (shown as near or substantially adjacent) the encased end 111b of the air flow sleeve 110. FIG. 8 shows a similar embodiment in which a single grouping of apertures 112 is positioned towards the longitudinal middle of the air flow sleeve 110. Alternative embodiments could include single groupings of apertures 112 at any point along the length of the air flow sleeve 110. FIG. 5 shows an alternative preferred embodiment of the invention having a plurality of groupings of apertures 112 on the air flow sleeve 110. FIG. 6 shows another alternative preferred embodiment of the invention having a plurality of substantially evenly spaced apertures 112 on the air flow sleeve 110. FIG. 7 shows yet another alternative preferred embodiment of the invention having a having groupings of apertures 112 on the longitudinal sides (or edges—as opposed to the faces) of the air flow sleeve 110 at the encased end 111b of the air flow sleeve 110. FIGS. 9-11 show that the apertures 112 on only the top sleeve sheet 110a or on both the top sleeve sheet 110a and the bottom sleeve sheet 110b (either directly opposite each other as in FIG. 10 or staggered as in FIG. 11).

Experimental use has shown significant advantages embodiments that include single groupings of apertures 112 (e.g. FIGS. 4 and 8) at any point along the length of the air flow sleeve 110. One reason for this effectiveness is that the air flows at maximum pressure to a single point of the cast system 140 and then escapes the cast system 140. For example, in a leg cast, putting an aperture grouping at the top of the ankle would force the air to flow upward along the length of the cast. In another example, strategically putting an aperture grouping at the bend of an elbow on an arm cast would force the air to flow both upward (toward the shoulder) and forward (toward the wrist) thereby forcing air along the length of the cast.

Variations on the size of the apertures 112, the shape of the apertures 112, the arrangement of the apertures 112, and quantity of the apertures 112 would depend on many variables including, but not limited to the user, the injury, the location of the injury (e.g. arm, wrist, leg), and the air supply. For example, it should be noted that a single large aperture 112 may be used in place of the aperture grouping.

Separator

Preferred embodiments of the present invention include a separator 114. In one preferred embodiment the separator 114 is a flexible member that is at least partially longitudinally coextensive with the air flow sleeve 110. To allow for expansion of the air flow sleeve 110 when it is inflated, the exterior circumference of the separator 114 is preferably at least slightly smaller than the interior circumference of the air flow sleeve 110. In other words, the separator 114 is slightly narrower and/or shorter than the air flow sleeve 110.

The first main purpose for the separator 114 is that it is used to hold the air flow sleeve 110 when it is positioned within the cast system 140. The inflation and de-inflation of the air flow sleeve 110 without a separator 114 can allow the air flow sleeve 110 to become loose, become unaligned, can "ride up" and/or otherwise become "mal-positioned." Using a separator 114 within the air flow sleeve 110, however, prevents this problem. Further, in some embodiments in which there is some adjustability in the positioning of the air flow sleeve system 100, the separator 114 provides the necessary stiffness to allow movement of the air flow sleeve 110. For example, a user could slightly tilt the air flow sleeve system 100 so that the apertures 112 were directed towards the front of the cast system 140 or towards the back of the cast system 140. Without the separator 114, this repositioning would be impossible. Still further, use of a separator 114 make it possible for removal and replacement of the air flow sleeve system 100.

The second main purpose for the separator 114 is that it is used to prevent the top and bottom "sleeve sheets" 110a, 110b of the air flow sleeve 110 from sticking together. Just the presence of the separator 114 is a deterrent for the top and bottom "sleeve sheets" 110a, 110b of the air flow sleeve 110 sticking together. Further, the stiffness of the separator 114 allows a user to "wiggle" the air flow sleeve 110 to "un-stick" the top and bottom "sleeve sheets" 110a, 110b of the air flow sleeve 110.

The separator 114 may "float" freely within the air flow sleeve 110. Alternatively, preferred embodiments of the separator 114 may be adapted to fit within, fit around, and/or mate with the retaining device 116 (or other connection apparatus) and/or the coupler 120.

The material from which the separator 114 is constructed is preferably stiffer than the material from which the air flow sleeve 110 is constructed. It should be noted, that the material from which the separator 114 is to be constructed may be plastic, rubber, or other materials that are suitably flexible, shape-conformable, durable, and/or of the appropriate medical grade or having the appropriate qualities necessary for fulfilling its function. It should be noted that the material preferably is also at least somewhat shape-retainable so that, even if bent or flattened, it generally returns to its original shape.

Retaining Device

Most of the figures also show the use of a retaining device 116 (or other connection apparatus) that is preferably included at the accessible end 111a of the air flow sleeve 110 to connect the air flow sleeve system 100 to the air producing mechanism 130. There are many variations of the retaining device 116 including, but not limited to a spring embodiment (FIGS. 2, 3, 4, 9, and 12), a tubular embodiment (FIGS. 7 and 8), and a reinforcement embodiment (FIGS. 5 and 10). Also, the positioning of the retaining device 116 has many variations including within the accessible end 111a of the air flow sleeve 110 (FIGS. 4, 7, 9, and 12), outside of the accessible end 111a of the air flow sleeve 110 (FIGS. 6 and 8), and coextensive with the accessible end 111a of the air flow sleeve 110 (FIGS. 5 and 10).

One purpose of the retaining device 116 is to hold the air flow sleeve 110 open for the coupler 120 so that it can be easily inserted (and allow for removal and/or replacement).

Another purpose of the retaining device 116 is that it may function as a connection mechanism to which the coupler 120 can be temporarily (i.e. for removal and/or replacement) or permanently attached. This will be discussed in more detail in connection with the coupler 120. For example, embodiments of the reinforcement retaining device 116 could have connection means on their annular inner surface, their annular outer surface, or their annular rim edge that would be suitable for connecting to the coupler 120 or directly or indirectly to the air producing mechanism 130. Alternatively, the retaining device 116 may function like a rubber band so as to self-secure itself to other components (e.g. the coupler 120).

The material from which the retaining device 116 is constructed may be stiffer than the material from which the air flow sleeve 110 is constructed, although flexibility or "give" would be advantageous for the purpose of providing comfort to the user. It should be noted, that the material from which the retaining device 116 is to be constructed may be plastic, rubber, or other materials that are suitably flexible, shape-conformable, durable, and/or of the appropriate medical grade or having the appropriate qualities necessary for fulfilling its function. It should be noted that the material preferably is also at least somewhat shape-retainable so that, even if bent or flattened, it generally returns to its original shape.

Exemplary Embodiments of Air Flow Sleeve System

FIGS. 4-12 show some alternative embodiments of the inflatable air flow sleeve system 100 of the present invention. These alternative embodiments are meant to be exemplary and are not meant to limit the scope of the invention.

FIG. 4 shows a first preferred embodiment of an inflatable air flow sleeve system 100. This exemplary embodiment is shown as having a single grouping of apertures 112 at (shown as near or substantially adjacent) the encased end 111b of the air flow sleeve 110. This exemplary embodiment is also shown as having an interior spring retaining device 116a. The interior spring retaining device 116a could be replaced by any device suitable for fulfilling the purposes of the retaining device as described above.

FIG. 5 shows a second preferred embodiment of an inflatable air flow sleeve system 100. This exemplary embodiment is shown as having a plurality of groupings of apertures 112 on the air flow sleeve 110. This exemplary embodiment is also shown as having a reinforcement retaining device 116b. Embodiments of the reinforcement retaining device 116b could have connection means on their annular inner surface, their annular outer surface, or their annular rim edge that would be suitable for connecting to the coupler 120 or directly or indirectly to the air producing mechanism 130. The reinforcement retaining device 116b could be replaced by any device suitable for fulfilling the purposes of the retaining device as described above.

FIG. 6 shows a third preferred embodiment of an inflatable air flow sleeve system 100. This exemplary embodiment is shown as having a plurality substantially evenly spaced apertures 112 on the air flow sleeve 110. One problem with this embodiment is the likelihood that the air pressure will tend to vary along the length of the air flow sleeve. This exemplary embodiment is also shown as having an exterior spring retaining device 116c. The exterior spring retaining device 116c could be replaced by any device suitable for fulfilling the purposes of the retaining device as described above.

FIG. 7 shows a fourth preferred embodiment of an inflatable air flow sleeve system 100. This exemplary embodiment is shown as having groupings of apertures 112 on the longitudinal sides (edges, as opposed to faces) of the air flow sleeve 110 at the encased end 111b of the air flow sleeve 110. This exemplary embodiment is also shown as having an interior alternative retaining device 116d shown as a tubular member. The interior alternative retaining device 116d could be replaced by any device suitable for fulfilling the purposes of the retaining device as described above.

FIG. 8 shows a fifth preferred embodiment of an inflatable air flow sleeve system 100. This exemplary embodiment is shown as having a single grouping of apertures 112 positioned towards the longitudinal middle of the air flow sleeve 110. Alternative embodiments could include single groupings of apertures 112 at any point along the length of the air flow sleeve 110. This would be particularly suitable for use with cast systems in which there was a bend (e.g. at the ankle of leg cast, at the wrist of an arm cast, or at the elbow of an arm cast). This exemplary embodiment is also shown as having an exterior alternative retaining device 116e shown as a tubular member. The exterior alternative retaining device 116e could be replaced by any device suitable for fulfilling the purposes of the retaining device as described above.

FIG. 9 shows a preferred embodiment of an inflatable air flow sleeve system 100. This exemplary embodiment is shown as having a single grouping of apertures 112 in the top sleeve sheet 110a at the encased end 111b of the air flow sleeve 110.

FIG. 10 shows a preferred embodiment of an inflatable air flow sleeve system 100. This exemplary embodiment is shown as having groupings of apertures 112 in the top sleeve sheet 110a and the bottom sleeve sheet 110b at the encased end 111b of the air flow sleeve 110, the grouping of apertures 112 in the top sleeve sheet 110a being directly opposite the grouping of apertures 112 the bottom sleeve sheet 110b.

FIG. 11 shows a preferred embodiment of an inflatable air flow sleeve system 100. This exemplary embodiment is shown as having groupings of apertures 112 in the top sleeve sheet 110a and the bottom sleeve sheet 110b at the encased end 111b of the air flow sleeve 110, the grouping of apertures 112 in the top sleeve sheet 110a being staggered from the grouping of apertures 112 the bottom sleeve sheet 110b.

Figure 12:
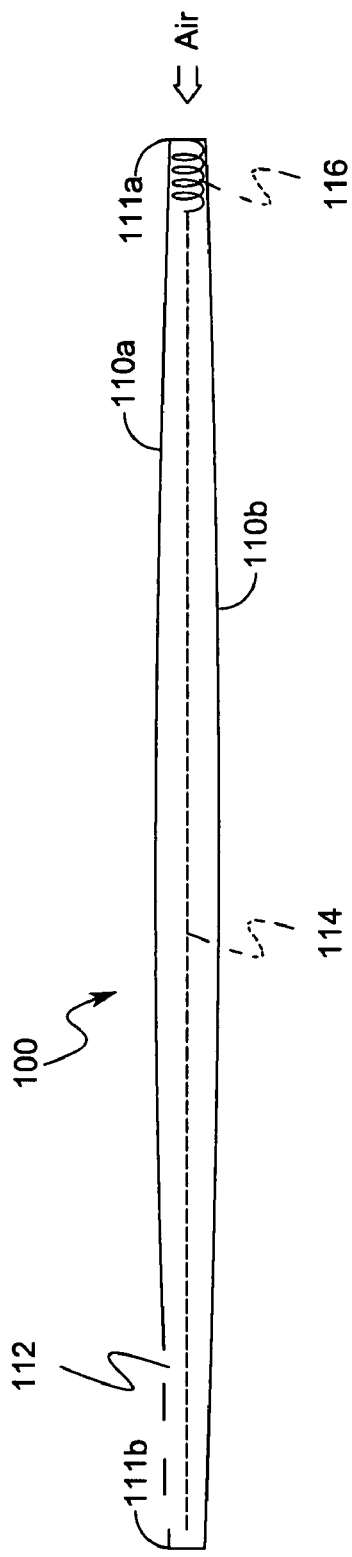
FIG. 12 is a side view of an exemplary preferred embodiment of an inflatable air flow sleeve system of the present invention in an inflated stated.

FIG. 12 shows a preferred embodiment of an inflatable air flow sleeve system 100 of the present invention in an inflated stated.

Coupler

Figure 2:
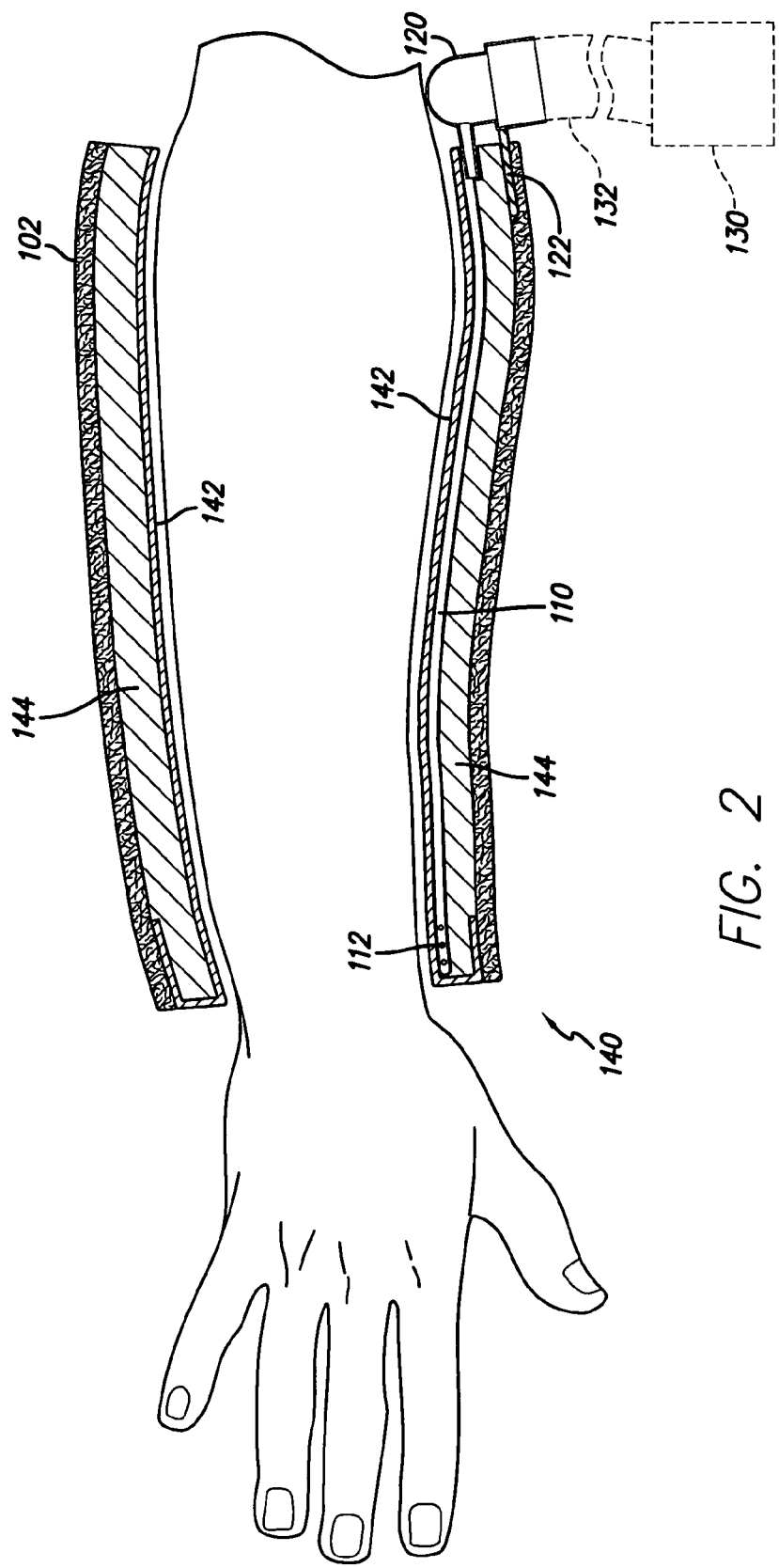
FIG. 2 is a cross-sectional view of an exemplary preferred embodiment of an air flow sleeve system of the present invention, the air flow sleeve system positioned between a limb and a cast surrounding the limb.
Figure 3:
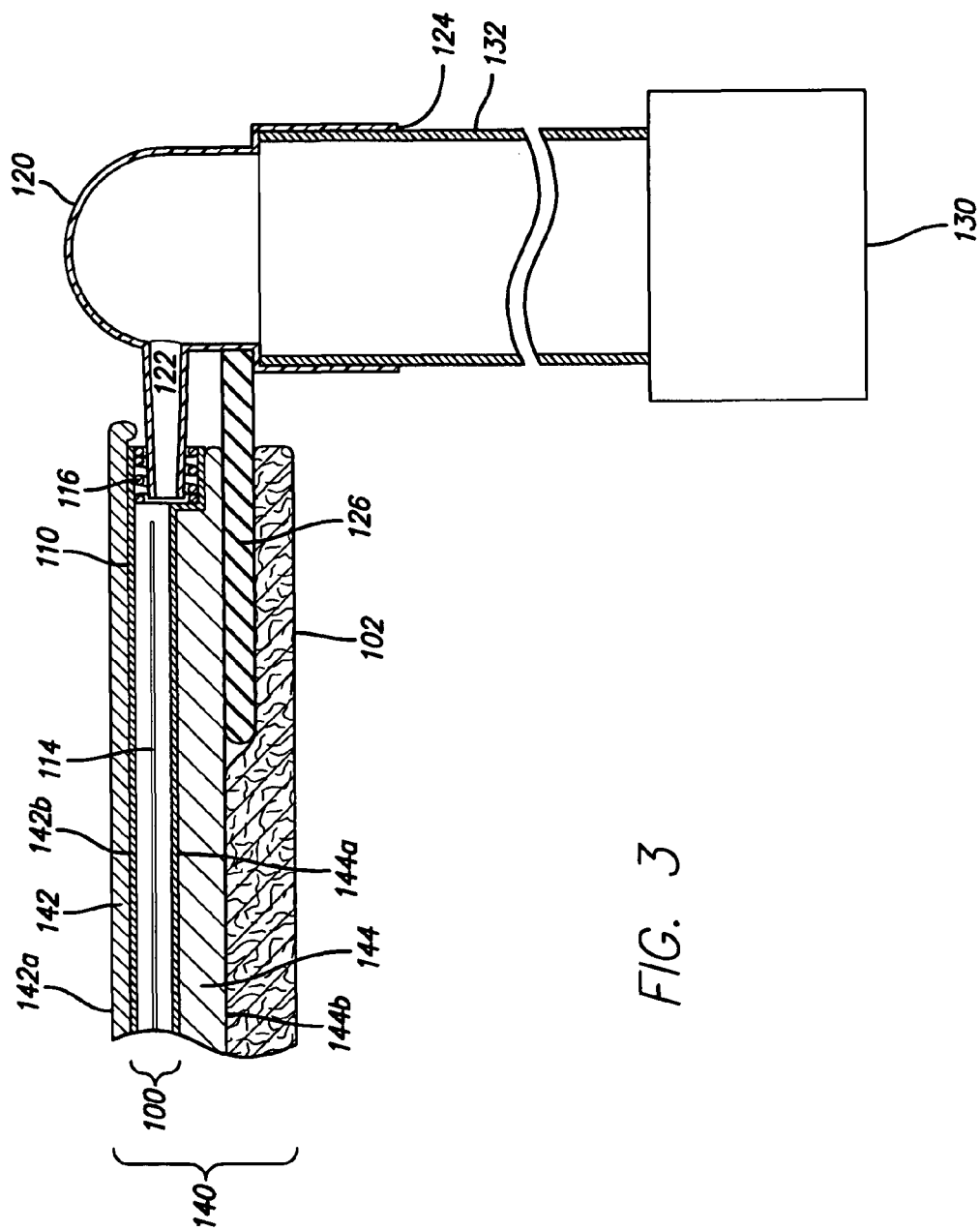
FIG. 3 is an enlarged cross-sectional view of one end of an exemplary preferred embodiment of an air flow sleeve of the present invention connected to an exemplary unique coupler.

The unique coupler 120, as shown in FIGS. 1-3, is preferably used to functionally connect (e.g. so that air flows through) the accessible end 111a of the air flow sleeve 110 directly or indirectly to an air producing mechanism 130. There may be additional air transmitting structure 132 (e.g. plastic or rubber surgical tubing or hosing) between the coupler 120 and the air flow sleeve 110 and/or between the coupler 120 and the air producing mechanism 130. The connections between the coupler 120 and the air flow sleeve 110 and between the coupler 120 and the air producing mechanism 130 may be simple connection means (e.g. friction fits and/or press fits). Alternatively more complicated connection means (e.g. using threading or additional securing apparatus) may be used.

The unique coupler 120, as shown in FIGS. 1-3, has an output sleeve end 122 and an input air insertion end 124. The output sleeve end 122 of said coupler 120 is connectable to the accessible end 111a of the air flow sleeve 110. The input air insertion end 124 of the coupler 120 is functionally connectable (e.g. directly or indirectly) to the air producing mechanism 130. The shown coupler 120 is "L-shaped," but this is an exemplary embodiment that could be changed depending on factors such as where the coupler 120 is to be positioned and with which limb the coupler 120 is to be associated.

The shown unique coupler 120 preferably includes a stabilizing protrusion 126 (shown as a flexible flap), that significantly enhances the present invention. The stabilizing protrusion 126 is used to attach (temporarily or permanently) or incorporate (temporarily or permanently) the coupler 120 to the casting system 140. As will be discussed below, the stabilizing protrusion 126 is preferably positioned within (incorporated or integrated) the casting system 140. In one preferred embodiment, the stabilizing protrusion 126 is positioned during the process of creating the cast system 140 and thus becomes affixed to the casting material 102. This is a significant mechanism for holding the coupler 120 steady in relation to the casting material 102. If the stabilizing protrusion 126 is flexible, the coupler 120 may move slightly in relation to the casting material 102 which may be beneficial for user comfort and/or for ease of use (e.g. for hooking up the air producing mechanism 130).

It should be noted that the stabilizing protrusion 126 may be integral with, attachable to, and/or removable from the coupler 120. If the stabilizing protrusion 126 is removable from the coupler 120, the coupler 120 may be replaced if desired. Accordingly, a connection joint (not shown) may be positioned between the coupler 120 and the stabilizing protrusion 126. In preferred embodiments in which the stabilizing protrusion 126 is removable from the coupler 120 and there is a separator 114 within the air flow sleeve 110, not only can the coupler 120 be replaced, but the entire air flow sleeve system 100 can be slid out of the cast system 140 and replaced because preferred embodiments of the separator 114 provide enough stiffness to allow gentle reinsertion of the air flow sleeve system 100 between the comfort layer 142 and the backing/padding layer 144 of the cast system 140.

Structure may also be provided so that the coupler 120 is integral with, attachable to, and/or removable from the output sleeve end 122 of the air flow sleeve system 100. As discussed, friction fits, press fits, and threading may be used as connection means. In addition, a retaining device 116 (or other connection apparatus) may be used as a means for connection. Additional and/or alternative connection means may be used to attach the output sleeve end 122 to the coupler 120. For example, an exterior alternative retaining device (e.g. a tubular member or band) may be used to annularly removably (temporarily) secure the accessible end 111a of the air flow sleeve 110 to the output sleeve end 122 of the coupler 120. Another example would be to use adhesive to annularly "permanently" secure the output sleeve end 122 to the accessible end 111a of the air flow sleeve 110. Whatever means is used for securing, it should be "air tight" or substantially "air tight." It should also be noted that the accessible end 111a of the air flow sleeve 110 may be inserted into in the interior of the output sleeve end 122 as opposed to being positioned on annularly around the exterior of the output sleeve end 122.

Without repetition, it should be understood that similar connection schemes discussed in the above paragraph may be used between the input air insertion end 124 of the coupler 120 and the air transmitting structure 132 or the air producing mechanism 130.

The coupler 120 is preferably relatively stiff and shape-retainable, although some flexibility or "give" would be advantageous for the purpose of providing comfort to the user. It should be noted, that the material from which the coupler 120 is to be constructed may be plastic, rubber, or other materials that are suitably stiff, shape-retainable, durable, and/or of the appropriate medical grade or having the appropriate qualities necessary for fulfilling its function. It should be noted that the stabilizing protrusion 126 may be made of a different material that is more flexible than the rest of the coupler 120 and/or there may be a joint (e.g. a hinge, a ball joint, or a flexible portion) between the stabilizing protrusion 126 and the coupler 120.

Air Producing Mechanism

In preferred embodiments the air producing mechanism 130 (e.g. a compressor, air pump, and/or blower) is extremely compact, light-weight, quiet, and energy efficient. In one preferred embodiment a pump is used because it can provide air through a small tubing system and can be built relatively small as compared to alternative air producing mechanisms. Preferred embodiments of the invention can be attached directly to the cast system 140, attached directly to the patient, attached directly to the patient's clothes, and/or transportable in a patient's pocket, purse, or specially designed pouch. The air producing mechanism 130 may be attached directly or indirectly to the coupler 120. If it is attached indirectly, air transmitting structure 132 (e.g. plastic or rubber surgical tubing or hosing) may be used to make the connection. The air producing mechanism 130 preferably provides forced air at approximately 40 degrees to 70 degrees. Preferably, the air is cool. Exemplary preferred embodiments of the air producing mechanism 130 provide between approximately two (2) cubic feet per minute of air flow and approximately ten (10) cubic feet per minute of air flow. Other exemplary embodiments provide air at a rate of between 20-25 psi (e.g. 28 psi). Alternative preferred embodiments provide a variable flow. Preferred embodiments of the air producing mechanism 130 have a power requirement of 110 amps or three (3) to twelve (12) volts. The air producing mechanism 130 is preferably battery operated. The batteries are preferably rechargeable. The preferred embodiments of the invention can be used almost anywhere and at almost any time.

Cast Structure Incorporating Air Flow Sleeve System

As shown in FIG. 2, in one preferred embodiment, the air flow sleeve system 100 is positioned within a cast system 140 to form a unique cast structure. The cast system 140 includes casting material 102, a comfort layer 142 (shown as a porous comfort sleeve that lies against a patient's skin), and a backing/padding layer 144 (shown as a thick cotton layer). The air flow sleeve system 100 is preferably positioned between the comfort layer 142 and the backing/padding layer 144. The comfort layer 142 may be known casting products (e.g. orthopedic stockinettes) or may be a specialized product made from cotton, synthetic materials, or other materials having the necessary characteristics to satisfy its intended purpose. The backing/padding layer 144 may be known orthopedic stockinettes, synthetic materials, waterproof liners, or other materials having the necessary thickness, compressibility, and other characteristics to satisfy its intended purpose. As discussed, the backing/padding layer 144 is preferably relatively thick to allow for expansion and compaction. Casting materials 102 (such as plaster structure or fiberglass structure) surround the backing/padding layer 144. The air flow sleeve system 100 is positioned so that the accessible end 111a is accessible from the top edge (the rim) of the cast system 140. The accessible end 111a of the air flow sleeve system 100 may be functionally connected (e.g. directly or indirectly) to an air producing mechanism 130.

Preferred embodiments of the present invention incorporate the backing/padding layer 144 described above. The backing/padding layer 144 provides a cushion of variable thickness such that it compresses (compacts) to allow the air flow sleeve 110 to expand and expands to ensure proper fit of the cast system 140 when the air flow sleeve 110 is in the compacted/un-inflated state. The backing/padding layer 144 separates the air flow sleeve 110 from the casting material 102 so that the air flow sleeve 110 can be slid out of and reinserted into the cast system 140. The backing/padding layer 144 also provides protection to the user from the heat (and possible burns) from the plaster and/or fiberglass which are usually quite hot.

Figure 13:
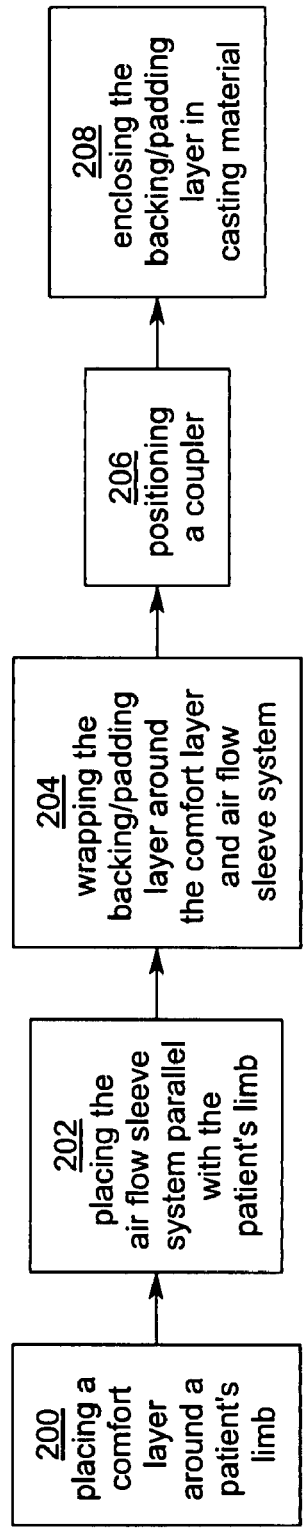
FIG. 13 is a simplified flow chart of an exemplary preferred embodiment of the method for constructing the cast structure of the present invention.

One exemplary preferred embodiment of a method of creating a cast system 140 of the present invention is shown in FIG. 13. In this exemplary method the cast system 140 may be formed using the following exemplary steps:

(200) placing a comfort layer 142 around a patient's limb such that an annular inner surface 142a of the comfort layer 142 is annularly adjacent (facing) the limb and the annular outer surface 142b of the comfort layer 142 is annularly remote from (facing away from) the limb;

(202) placing the air flow sleeve system 100 substantially parallel with the patient's limb so that at least one end 111a is accessible from an edge of the cast system 140, the second end to be encased in the cast system 140;

(204) placing (e.g. by wrapping) the backing/padding layer 144 around the comfort layer 142 and air flow sleeve system 100 so that the backing/padding layer 144 at least partially surrounds the comfort layer 142 and air flow sleeve system 100 with an annular inner surface 144a of the backing/padding layer 144 is annularly adjacent (facing) the comfort layer 142 (and air flow sleeve system 100) and the annular outer surface 142b of the backing/padding layer 144 is annularly remote from (facing away from) the comfort layer 142 (and air flow sleeve system 100);

(206) positioning a coupler 120 such that the output sleeve end 122 is associated with the accessible end 111a of the air flow sleeve 110 and the stabilizing protrusion 126 is above (distal from the limb) the backing/padding layer 144; and (208) enclosing the backing/padding layer 144 in casting material 102 such that the stabilizing protrusion 126 is at least partially secured by the casting material 102.

It should be noted that some embodiments of the air flow sleeve system 100 and/or the coupler 120 (with or without the stabilizing protrusion 126) may be removable from and/or insertable into a cast system 140. In embodiments in which the stabilizing protrusion 126 is removable, the stabilizing protrusion 126 would not be secured by the casting material 102.

When air is injected into the air flow sleeve system 100 from the accessible end 111a, the air flow sleeve 110 at least partially inflates. Air would escape through the apertures 112 and be forced towards and around the limb through the porous comfort layer 142.

The terms and expressions that have been employed in the foregoing specification are used as terms of description and not of limitation, and are not intended to exclude equivalents of the features shown and described or portions of them. The scope of the invention is defined and limited only by the claims that follow.

What is claimed is:

1. An inflatable air flow sleeve system for injecting air flow from an air producing mechanism into a cast system, said air flow sleeve system comprising:
   (a) an inflatable air flow sleeve having a first accessible end and a second encased end;
   (b) at least one aperture through which air may flow, said at least one aperture defined by said air flow sleeve;
   (c) a separator positioned within said air flow sleeve, said separator at least partially longitudinally coextensive with said air flow sleeve; and
   (d) a coupler having an input air insertion end and an output sleeve end:
      (i) said output sleeve end of said coupler connectable to said first accessible end of said air flow sleeve; and
      (ii) said input air insertion end of said coupler functionally connectable to said air producing mechanism.

2. The air flow sleeve system of claim 1 further comprising a retaining device positioned at said first accessible end.

3. The air flow sleeve system of claim 1 wherein said at least one aperture is a plurality of apertures arranged in at least one grouping.

4. The air flow sleeve system of claim 1 wherein said at least one aperture is a plurality of apertures arranged in a grouping located substantially near said second encased end.

5. The air flow sleeve system of claim 1 wherein said at least one aperture is a plurality of apertures arranged in a grouping located substantially near the longitudinal middle of said air flow sleeve.

6. The air flow sleeve system of claim 1 wherein at least part of said coupler is integrated with said cast system.

7. The air flow sleeve system of claim 1 wherein said coupler further includes a protrusion, said protrusion being integrated with said cast system.

8. The air flow sleeve system of claim 7 wherein said protrusion is integral with said coupler.

9. The air flow sleeve system of claim 1, said cast system comprising casting material, a comfort layer, and a backing/padding layer.

10. A cast structure including an inflatable air flow sleeve for injecting air flow into said cast structure, said cast structure comprising:
   (a) a comfort layer at least partially annularly surrounding a limb, an annular inner surface of said comfort layer annularly adjacent said limb, an annular outer surface of said comfort layer annularly remote from said limb;
   (b) said inflatable air flow sleeve having at least one aperture defined by said air flow sleeve, said air flow sleeve positioned at least partially on said annular outer surface of said comfort layer, said air flow sleeve having a first accessible end and a second encased end;
   (c) a backing/padding layer at least partially annularly surrounding said air flow sleeve and said comfort layer;
   (d) casting material at least partially annularly surrounding said backing/padding layer, said air flow sleeve, and said comfort layer, wherein said casting material, said comfort layer, and said backing/padding layer form a cast system;
   (e) said first accessible end of said air flow sleeve accessible from said cast system;
   (f) an air producing mechanism directly or indirectly connected to said first accessible end of said air flow sleeve accessible from said cast system;
   (g) a coupler having an output sleeve end and an input air insertion end;
   (h) said output sleeve end of said coupler functionally connectable to said first accessible end of said air flow sleeve;
   (i) said input air insertion end of said coupler functionally connectable to said air producing mechanism; and
   (j) at least part of said coupler is integrated with said casting material of said cast system;
   (k) wherein air from said air producing mechanism flows into said air flow sleeve which expands, said backing/padding layer compacting to allow the expansion of said air flow sleeve.

11. The cast structure of claim 10 wherein said air flow sleeve further comprises a separator, said separator positioned within said air flow sleeve at least partially longitudinally coextensive with said air flow sleeve.

12. The cast structure of claim 10 wherein said at least one aperture is a plurality of apertures arranged in at least one grouping.

13. The cast structure of claim 10, said coupler further comprising a protrusion, said protrusion being integrated with said casting material of said cast system.

* * * * *